(12) United States Patent
Stephan et al.

(10) Patent No.: US 11,131,616 B2
(45) Date of Patent: Sep. 28, 2021

(54) ANALYZING FLUIDS

(71) Applicant: PerkinElmer Health Sciences Canada, Inc., Waltham, MA (US)

(72) Inventors: Chady Stephan, Brampton (CA); David Hilligoss, Venice, FL (US)

(73) Assignee: PerkinElmer Health Sciences Canada, Inc., Woodbridge (CA)

(*) Notice: Subject to any disclaimer, the term of this patent is extended or adjusted under 35 U.S.C. 154(b) by 61 days.

(21) Appl. No.: 16/629,063

(22) PCT Filed: Jan. 15, 2019

(86) PCT No.: PCT/US2019/013674
§ 371 (c)(1),
(2) Date: Jan. 7, 2020

(87) PCT Pub. No.: WO2020/149836
PCT Pub. Date: Jul. 23, 2020

(65) Prior Publication Data
US 2021/0223158 A1 Jul. 22, 2021

(51) Int. Cl.
*G01N 33/28* (2006.01)
*G01N 15/14* (2006.01)
*G01N 21/73* (2006.01)

(52) U.S. Cl.
CPC .......... *G01N 15/14* (2013.01); *G01N 21/73* (2013.01); *G01N 33/2858* (2013.01); *G01N 2015/1486* (2013.01)

(58) Field of Classification Search
CPC .. G01N 33/2888; G01N 21/29; G01N 21/251; G01N 21/293; G01N 21/534

USPC .......................................................... 356/70
See application file for complete search history.

(56) References Cited

U.S. PATENT DOCUMENTS

| | | | |
|---|---|---|---|
| 6,582,661 B1 | 6/2003 | Pardue et al. | |
| 6,928,861 B1 | 8/2005 | Rice | |
| 2001/0016706 A1* | 8/2001 | Leukanech | F04B 43/12 604/140 |
| 2001/0023130 A1* | 9/2001 | Gilton | G01N 1/32 438/689 |
| 2004/0087743 A1* | 5/2004 | Bai | C08F 210/18 526/74 |
| 2006/0263925 A1* | 11/2006 | Chandler | G01N 35/00871 438/61 |
| 2008/0209876 A1* | 9/2008 | Miller | H01M 10/052 55/522 |

(Continued)

OTHER PUBLICATIONS

Oct. 7, 2019, International Search Report and Written Opinion, PCT/US2019/013674.

*Primary Examiner* — Md M Rahman
(74) *Attorney, Agent, or Firm* — Banner & Witcoff, Ltd.

(57) ABSTRACT

A system and method of using the system for analyzing liquid samples obtain from viscous sources. The system includes a sample delivery system, a particle counter configured to receive a liquid sample from the liquid sample delivery system, a composition analyzer configured to receive the liquid sample from the particle counter, a feed system configured to draw the liquid sample through the particle counter and subsequently inject the liquid sample into the composition analyzer; and a processor to process and analyze data from the particle counter and composition analyzer.

18 Claims, 6 Drawing Sheets

(56) References Cited

U.S. PATENT DOCUMENTS

2016/0009557 A1* 1/2016 Harutyunyan ......... C01G 15/00
423/447.3
2016/0313237 A1 10/2016 Young et al.
2017/0322162 A1 11/2017 Park et al.

* cited by examiner

ANALYZING FLUIDS

CROSS-REFERENCE TO RELATED APPLICATIONS

This application is a U.S. National Stage application under 35 U.S.C. § 371 of International Application PCT/US2019/013674, filed Jan. 15, 2019. Benefit of the filing date of this prior application is hereby claimed. This prior application is hereby incorporated by reference in its entirety.

FIELD

Aspects described herein generally relate to integrated systems and methods for use analyzing liquid samples containing metals and other particles, and more particularly to instrumentation for analyzing particle content and elemental composition of samples such as lubricants, coolants, and similar fluids, as well as methods of processing those samples.

BACKGROUND

In industries such as mining, energy, and construction where heavy equipment is required for operations, maintenance of the equipment is an important part of operations. As the scale of operations increases, the size, complexity, and cost of the heavy equipment also increases. Equipment breakdown can be costly, with respect to both equipment repair and lost revenue from downtime. Consequently, preventative maintenance is important.

The particle content and elemental composition of key fluids, including oil, coolant, and other lubricants (such as hydraulic fluids, transmission fluids and gear oils), provides insight to the status of engines and other compartments. An increased concentration of particles and key wear metals provides an indication of the need for maintenance. Monitoring helps ensure that abrasive bearing wear is minimized, lubricants are clean enough for reliable operations, and the compartments of the heavy equipment are in generally good operating condition.

Particle counting is an important test for oil, coolant and lubricant analysis. Liquid particle counters are used to detect particulate contamination in the samples. The number and size distribution of particles in the sample typically are monitored as a measure of the cleanliness of the fluid. Particle counting instruments can be costly. Issues associated with handling of samples can limit the desirability and effectiveness of this analytical technique. For example, such samples are typically viscous and when analyzing samples directly without sample dilution, larger sample sizes typically are required (e.g., 20-40 mL of sample), the analysis time may be lengthy (e.g., 2-4 minutes per sample), and a large volume of solvent typically is required for rinsing the testing instrument between samples. Such extended processing and cleaning times may hinder the ability to quickly test samples in a cost-effective manner.

Other analytical techniques require that the sample introduced to the testing instrument is much less concentrated than the actual fluid to be tested. This requirement that the starting sample is diluted, sometimes very substantially, prior to analysis can be critical to the accuracy of the analytical technique. Despite its significance, a number of potential problems may hinder testing, including difficulties with handling and diluting the samples, slow throughput, and inconsistent results.

Analysis of liquid samples by inductively coupled plasma optical emission spectrometry device (ICP-OES) is the technique commonly used to monitor the elemental composition of liquid samples. Typically, a diluted sample fluid is nebulized into sample droplets in a spray chamber. The nebulized droplets are transported to, and injected into, a detector element of the analytical instrument. In ICP and other plasma sample analysis systems, the nebulized particles are injected into a high temperature plasma where they interact with energy present in the plasma to form fragments such as molecules, atoms and/or ions. Thus, the ability to properly and effectively process the sample to create nebulized sample droplets can have an impact on the further processing of the sample through the instrument and the quality of the results.

Typically, a sample will be sent to a particle counter, for example, and a separate sample will be diluted and sent to a composition analyzer such as ICP-OES. Current systems and analytical techniques do not provide efficient and cost-effective methods for testing samples of viscous fluids that contain particles, such as found in the mining, energy, construction, and power generation industries along with military applications, with consistent results.

SUMMARY

The following presents a simplified summary of various features described herein. This summary is not an extensive overview, and is not intended to identify required or critical elements or to delineate the scope of the claims. The following summary merely presents some concepts in a simplified form as an introductory prelude to the more detailed description provided below.

To overcome limitations in the prior art described above, and to overcome other limitations that will be apparent upon reading and understanding the present specification, aspects described herein are directed towards apparatuses and methods for analyzing samples of particle-containing fluids.

One or more embodiments include systems configured to analyze diluted samples taken from sources of viscous liquids. Such sources may comprise, for example, oil, coolant, or lubricant containing particulate contaminants. The sample analysis techniques may include counting and sizing individual particles of varying size in a liquid sample and identifying the concentrations of various elemental components present in the liquid sample.

A sample of a viscous liquid to be analyzed may be obtained and diluted in any suitable manner. In accordance with aspects of the invention, the diluted sample is delivered to a particle counter. The diluted sample is pulled through the particle counter via a feed system. The particle counter may include a measurement flow channel configured for particle counting analysis. The particle counter is a nondestructive measurement device that does not alter the characteristics of the particles in the diluted sample. Hence the same diluted sample may afterwards be analyzed in a different manner.

From the particle counter, the diluted sample passes to a composition analyzer such as an inductively coupled plasma optical emission spectrometry (ICP-OES) apparatus. The feed system facilitates flow of the diluted sample from the particle counter to the composition analyzer where the diluted sample is analyzed to determine the composition of the particles.

In certain aspects, the feed systems provide a very consistent flow rate of diluted sample through the particle counter and from the particle counter to the ICP-OES.

In certain aspects, the feed system comprises a syringe that pulls the sample through the particle counter into a sample loop and then injects the sample from the sample loop into the composition analyzer ICP-OES.

In other aspects, methods for analyzing samples from a viscous sample source are provided.

The systems and methods may be useful in testing samples from mining and heavy construction environments, as well as from automotive, power generation, avionics, pharmaceutical, semiconductor and other industries.

These and additional aspects will be appreciated with the benefit of the disclosures discussed in further detail below.

BRIEF DESCRIPTION OF THE DRAWINGS

A more complete understanding of aspects described herein and the advantages thereof may be acquired by referring to the following description in consideration of the accompanying drawings, in which like reference numbers indicate like features, and wherein.

DETAILED DESCRIPTION

In the following description of the various embodiments, reference is made to the accompanying drawings identified above and which form a part hereof, and in which is shown by way of illustration various embodiments in which aspects described herein may be practiced. It is to be understood that other embodiments may be utilized and structural and functional modifications may be made without departing from the scope described herein. Various aspects are capable of other embodiments and of being practiced or being carried out in various different ways.

As a general introduction to the subject matter described in more detail below, aspects described herein are directed towards apparatuses and methods for analyzing viscous samples containing particles, such as metal particles, by more than one testing component, where each testing component comprises a different analytical technique. The more than one testing component may be coupled with one another in an integrated system that provides a more efficient and cost-effective method of analyzing a liquid sample. Results are obtained relatively quickly and are more accurate and reproducible.

It is to be understood that the phraseology and terminology used herein are for the purpose of description and should not be regarded as limiting. Rather, the phrases and terms used herein are to be given their broadest interpretation and meaning. The use of "including" and "comprising" and variations thereof is meant to encompass the items listed thereafter and equivalents thereof as well as additional items and equivalents thereof. The use of the terms "mounted," "connected," "coupled," "positioned," "engaged," and similar terms, is meant to include both direct and indirect, as well as fixed or removable, mounting, connecting, coupling, positioning, and engaging by any suitable methods known to those of skill in the art. The terms "upstream" and "downstream" generally refer to the direction of liquid sample flow in the system. For example, a downstream component receives liquid sample from an upstream component.

An analytical instrument for testing liquid samples may be operated with one or more systems to test various characteristics of the samples in an integrated system. The analytical instrument is particularly useful for testing liquid samples containing metals and other particles, such as oil, coolant, or lubricant samples (hydraulic fluids, transmission fluids, and gear oils). Samples obtained from a source are typically viscous. Prior to utilizing the system presented herein, the samples are diluted. The present system is directed to analytical instruments such as particle counters and composition analyzers.

Figure 1:
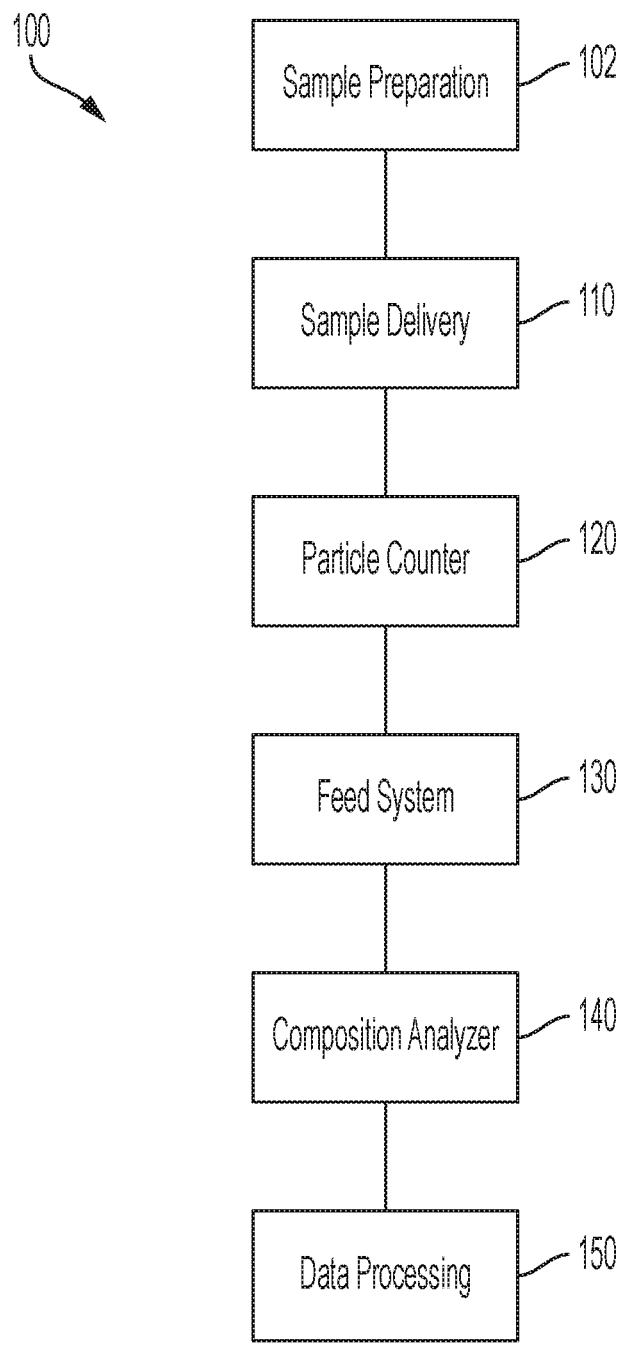
FIG. 1 is a block diagram of components of a system in accordance with one or more example embodiments.

As depicted in FIG. 1, a system 100 for analyzing a liquid sample may include sample preparation component 102, a sample delivery system 110, a particle counter 120, a feed system 130, a composition analyzer 140, and data processing component 150. In particular the sample delivery system 110, particle counter 120, feed system 130, and composition analyzer 140 work inline in a single system to achieve particle and elemental analysis in the same sample.

Although the elements of FIG. 1 are shown as block diagrams, the disclosure is not so limited. In particular, one or more of the boxes in FIG. 1 may be combined into a single box or the functionality performed by a single box may be divided across multiple existing or new boxes. For example, while the sample preparation 102 is visually depicted in FIG. 1 as being coupled proximate to sample delivery system 110, FIG. 1 contemplates that the sample source preparation 102 either may be positioned away, or spaced apart, from sample delivery system 110 or may occur offsite.

The sources of the samples include, but are not limited to, viscous liquids containing metals and other particles. The viscous liquid may be oil, lubricant, hydraulic fluid, and the like. In other aspects, samples may include emulsions, such as in pharmaceutical applications, coolants, and other fluids containing metal and other particles.

The viscous sample is diluted to a desired concentration. Such dilution may be conducted manually by an operator such as in small laboratories or by standalone diluter in high throughput laboratories. Calibration standards, carriers, and other fluids or substances also can be added to the sample for enhanced processing and generation of results. For example, one or more internal standards may be added to assist with calibrating one or more components of the system 100. In some aspects, sample preparation 102 includes a mixing chamber in which the sample is diluted to a desired ratio, such as by addition of a solvent. Dilution techniques and apparatus are known and any suitable dilution technique may be utilized. Importantly, a diluted sample is provided to the sample deliver system.

Suitable solvents for sample dilution include organic and aqueous solvents and the like, including kerosene or kerosene type solvents. Similar type solvent for other applications areas may be water based. The dilution ratio is suitable to provide a diluted sample of a concentration to render the diluted sample more flowable for subsequent processing and analysis in the system 100. In certain embodiments the dilution ratio of liquid sample to solvent is 1:10. As can be appreciated, however, the dilution ratio may be adjusted as needed to provide a liquid having viscosity and other flow characteristics suitable to pass through system 100, as desired. For example, the dilution ratio may be lower, such as 1:1, 1:5, or 1:10, or higher, such as 1:15, or 1:20, or in the range between 1:1 to 1:20, or between 1:5 to 1:15. A typical dilution ratio may be 1:10. Other dilution ratios also may be used depending on the initial viscosity and related properties of the liquid sample from the liquid sample source 102.

Dilution ratios depends on the viscosity of the initial sample and the desired viscosity entering the system. For example, solvents and hydraulics tend to be in the viscosity range of 2-10 cSt@40C. Engine oils are typically in the 10-80 cSt range. Other lubricants are up to about 700 cSt@40C. This viscosity is about as high as one would use with an automated system for doing the dilution. Any other lubricants (which there are quite a few) would be manually diluted weight to weight with a solvent. A 1/10 dilution would still work for these lubricants on this system for particle counters and ICP.

A diluted sample is easier to handle than a viscous sample due to its higher flowability and ability to pass through the system. Less sample is needed from the sample source. Further, less solvent is needed to clean the analyzers after sample testing.

The diluted samples are transferred to the sample delivery system 110 manually or automatically. For example, samples may be placed in an autosampler rack that is placed on an autosampler. For most busy labs, automated dilutors would dilute the samples directly in these racks that have the sample tubes already placed in it. When finished, the racks would then be manually moved from the dilutor to the autosampler. For manual dilution, the operator would dilute the samples into sample tubes then place the tubes into an autosampler rack.

The sample delivery system 110 can be any suitable system that delivers the diluted sample to the particle counter 120 in a consistent manner. The sample delivery system may include components, examples of which may be mechanical arms, pumps, tubing, valves, and the like, which are suitable for collecting a desired volume of diluted sample and introducing the sample to the first analytical apparatus 120. The sample delivery system may be manual or partially or completely automated.

In one aspect, the sample delivery system is an autosampler, such as CETAC 7400, 7600, or an equivalent thereof, which is typically equipped with a stirrer to homogenize the sample prior to analysis, a syringe pump module, and a meshed probe to prevent fibers or other contaminants from clogging the equipment, e.g. tubes. The particle counter may be mounted on top of the autosampler Z drive.

The particle counter 120 may be any suitable instrument configured to detect particle characteristics (e.g., number, size, and distribution) of the diluted sample, for example the particle counter may include a measurement flow channel configured for particle counting analysis. Suitable particle counters are pore blockage particle counters, light blocking-type particle counters, and laser direct imaging particle counters. Suitable particle counters are described, for example, in U.S. Pat. Nos. 5,835,211 and 6,794,182. Suitable particle devices are commercially available such as particle counters manufactured by PSS or PerkinElmer. As noted above, the particle counter may be mounter on the autosampler.

Figure 2:
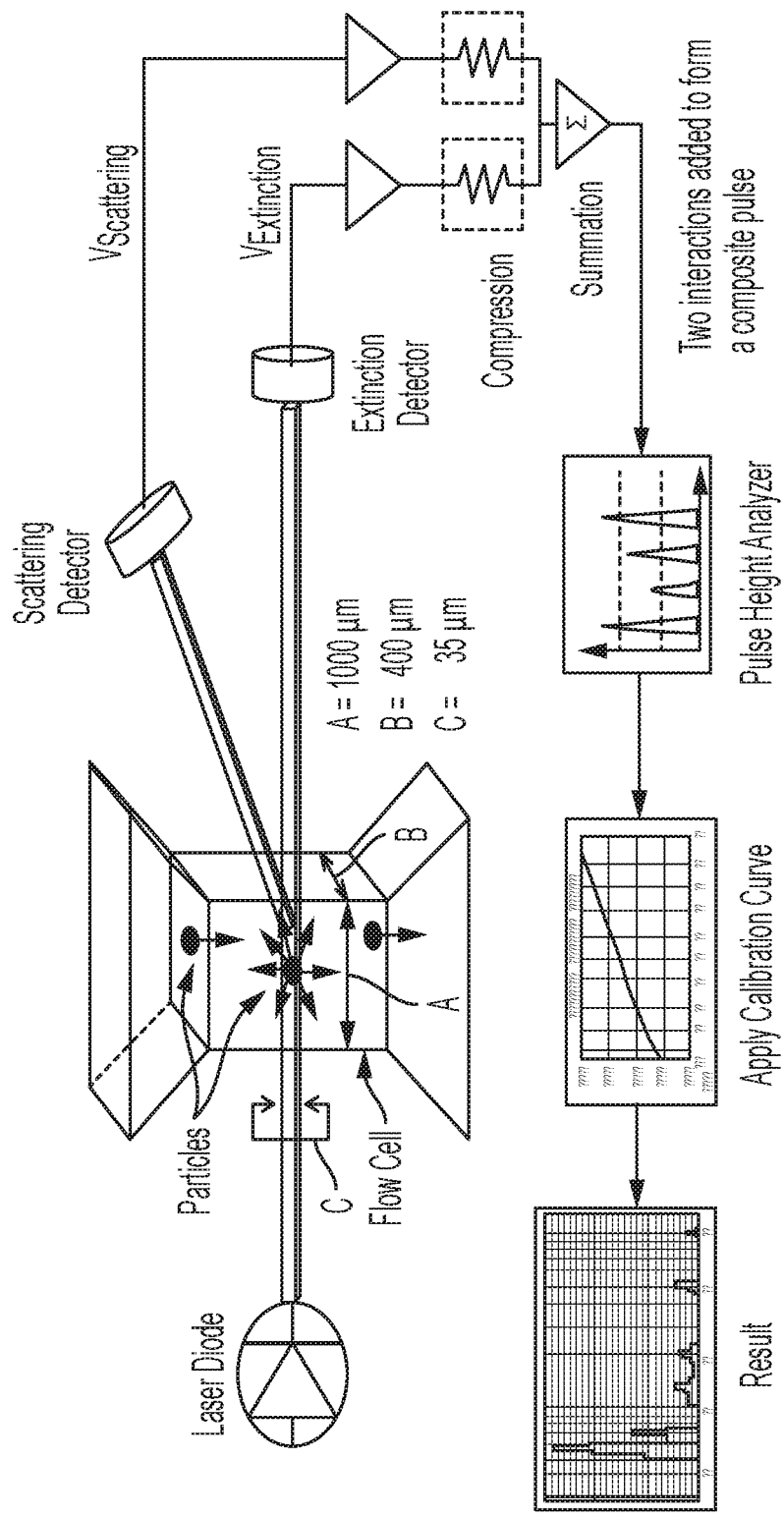
FIG. 2 depicts a schematic of a particle counter and its process in accordance with one or more example embodiments.

In certain aspects, the first analytical apparatus 120 includes a light blocking-type particle counter as seen in FIG. 2. A liquid sample flows through the cell of a sensor as a laser is shined through the sample. Depending on the mode of the sensor the amount of light that is blocked by the particles in the liquid (extinction mode) are measured and the light that is scattered by the particles in the liquid (summation mode) are measured in pulses. Pulses from the sensor are sent to a pulse height analyzer (counter) that converts pulses to particle size through the use of a calibration curve. These raw counts are then converted into a particle count concentration (particle count per ml) by taking into account the flowrate of the system and the measurement time per replicate.

Importantly, the particle counter 120 is non-destructive diluted sample. In other words, the diluted sample entering the particle counter exits the particle counter unchanged so that is essentially the same diluted sample that is then introduced into the composition analyzer 140 subsequently.

From the particle counter 120, the sample passes to the composition analyzer 140, which may be any suitable instrument to provide an elemental composition analysis of the sample. A suitable composition analyzer includes, but not limited to, an inductively coupled plasma optical emission spectrometry (ICP-OES) component.

The feed system 130 draws the diluted sample through the system 100 and provides a consistent flow rate of diluted sample through the particle counter 120 to the composition analyzer 140. In certain aspects, the feed system 130 includes a pump (with a sample loop) disposed between the particle counter 120 and the composition analyzer 140 and may also include additional pumps and/or ancillary components in-line between the particle counter 120 and composition analyzer 140.

The flow rate of sample is generally maintained by the feed system using a suitable mechanical pump or pumps, e.g., a vacuum pump, rotary pump, or syringe-drive pump, or combinations thereof. In certain instances, a syringe-drive pump is used to pull the diluted sample from the autosampler through the particle counter 120 to the feed mechanism of the composition analyzer 140. A steady flow rate of liquid sample through system 100 provides more consistent data and correlation of data between particle counter 120 and composition analyzer 140, which in turn provides improved results for the analysis of the liquid sample. A suitable feed system is Particle Xpress by CETAC which includes a control tower and a position injection valve, a 10 ml syringe drive.

The feed system 130 injects the diluted sample into the composition analyzer 140 along with a carrier. The sample loop is filled with sample after the particle counting cell, then the loop changes to inject so a carrier is needed to push the diluted sample into the nebulizer and the sample introduction system of the ICP. The carrier is typically the solvent used to dilute the ICP standards and samples. The internal standard spiked into the dilution solution is not needed to be part of the carrier solution. Suitable carriers include, but are not limited to kerosene or kerosene-based solvents.

As noted, the composition analyzer may be an ICP-OES device. The ICP-OES couples an inductively coupled plasma ionization source to an optical emission spectrometer. Briefly, a sample, most commonly an aerosol produced by nebulization, is injected into a high temperature atmospheric pressure plasma obtained by the coupling of radio frequency (rf) energy into the flowing argon gas stream. The resultant plasma is characterized by a high temperature (about 7000K) and relatively high concentration (about $10^{15}$ $cm^{-3}$) of equal numbers of electrons and positive ions. Provided that the particles of the nebulized sample are small enough, as described above, the sample is promptly vaporized, atomized and ionized as it flows through the plasma.

As noted, samples are introduced into argon plasma as aerosol droplets. The plasma dries the aerosol, dissociates the molecules, forms ground state atoms and then multiple forms of excited atom and/or ions for each element.

Some ICP-OES instruments include the following components: a sample introduction system composed of a nebulizer and spray chamber; an ICP torch and RF coil for generating the argon plasma that serves as the atom and ion source; an optical spectrometer, which detects the emission from excited atoms and/or ions and a data handling and system controller that controls aspects of instrument control and data handling for use in obtaining final concentration results.

Detection of the emission from excited neutral atoms and ions in the ICP provides for the quantitative determination of the elemental composition of the sample. Many current ICP-OES instruments provide array detection for true simultaneous determination across most of the periodic table.

Components in the composition analyzer 140 to vaporize, atomize, and ionize the sample particles may include glow discharge, graphite furnace, and capacitively coupled plasma devices, or other suitable devices. Preferably, the components to vaporize, atomize and ionize the particles includes an inductively coupled plasma (ICP) device that has a capacity to disintegrate, vaporize, atomize and ionize cells during their short residence time in the plasma. Other advantages of ICP are that it is particularly tolerant of concomitant materials, is robust to changes of the composition of the plasma gases, and is a highly efficient atomizer and ionizer.

It should be understood that the term "components to vaporize, atomize, and excite or ionize" includes components where atomization may not be necessary, so that the term may or may not encompass vaporization followed by ionization directly. In some applications, such as for example optical emission spectrometry (OES), it is not essential to ionize the sample; emission from atomic species can be sufficient. For OES, it is necessary only to excite the atoms (or ions) to cause emission. Thus, for example, "vaporize, atomize, and ionize" should be understood to mean vaporize, atomize and ionize or excite (either or both atoms and ions) for OES.

In operation, the composition analyzer 140 described herein may be calibrated using liquid standards according to calibration techniques known to those of skill in the art. The systems may be operated with liquid samples and calibrated using liquid standards.

Figure 3:
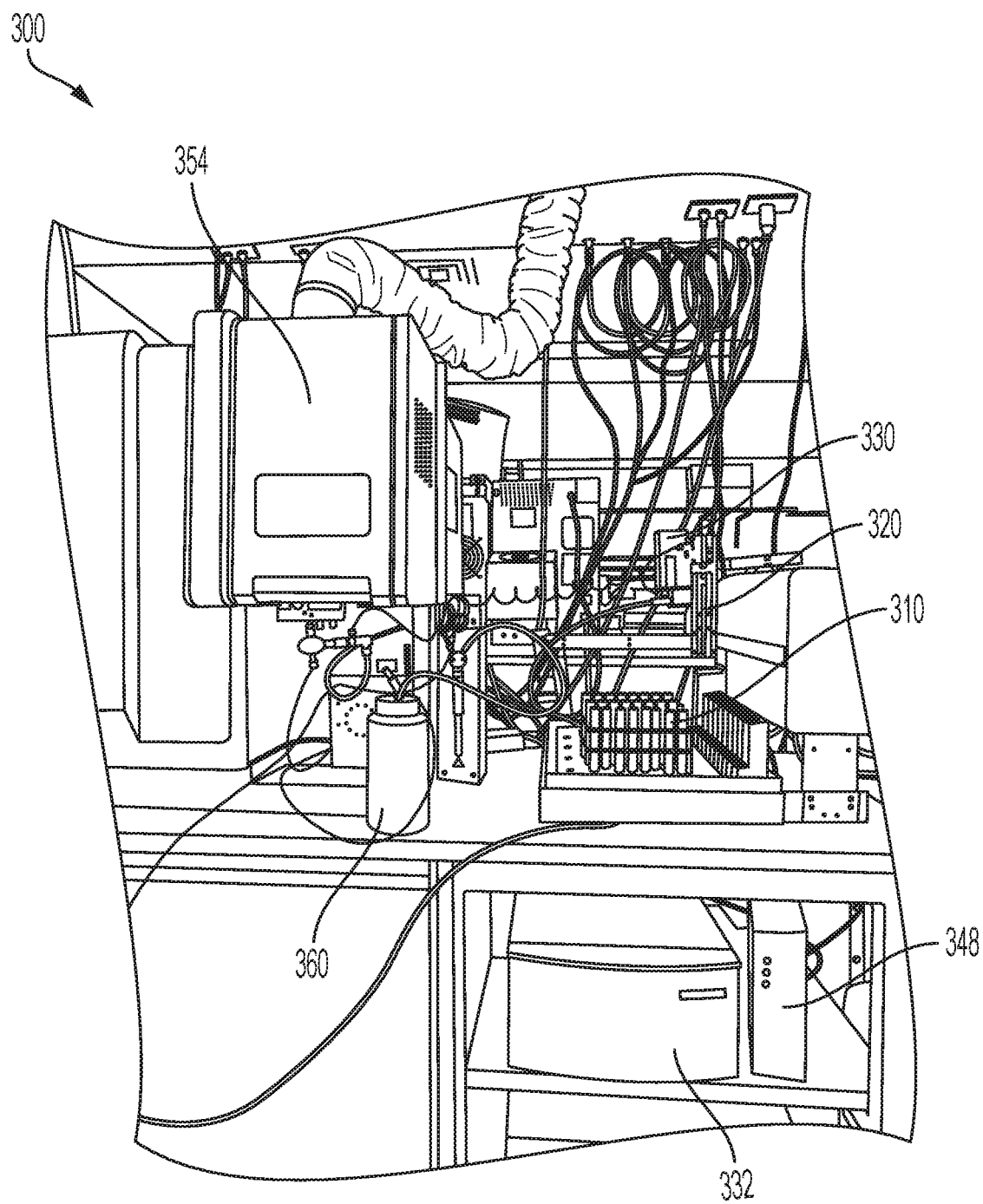
FIG. 3 depicts particle and elemental particle analyzers in a same system in accordance with one or more example embodiments.
Figure 3A:
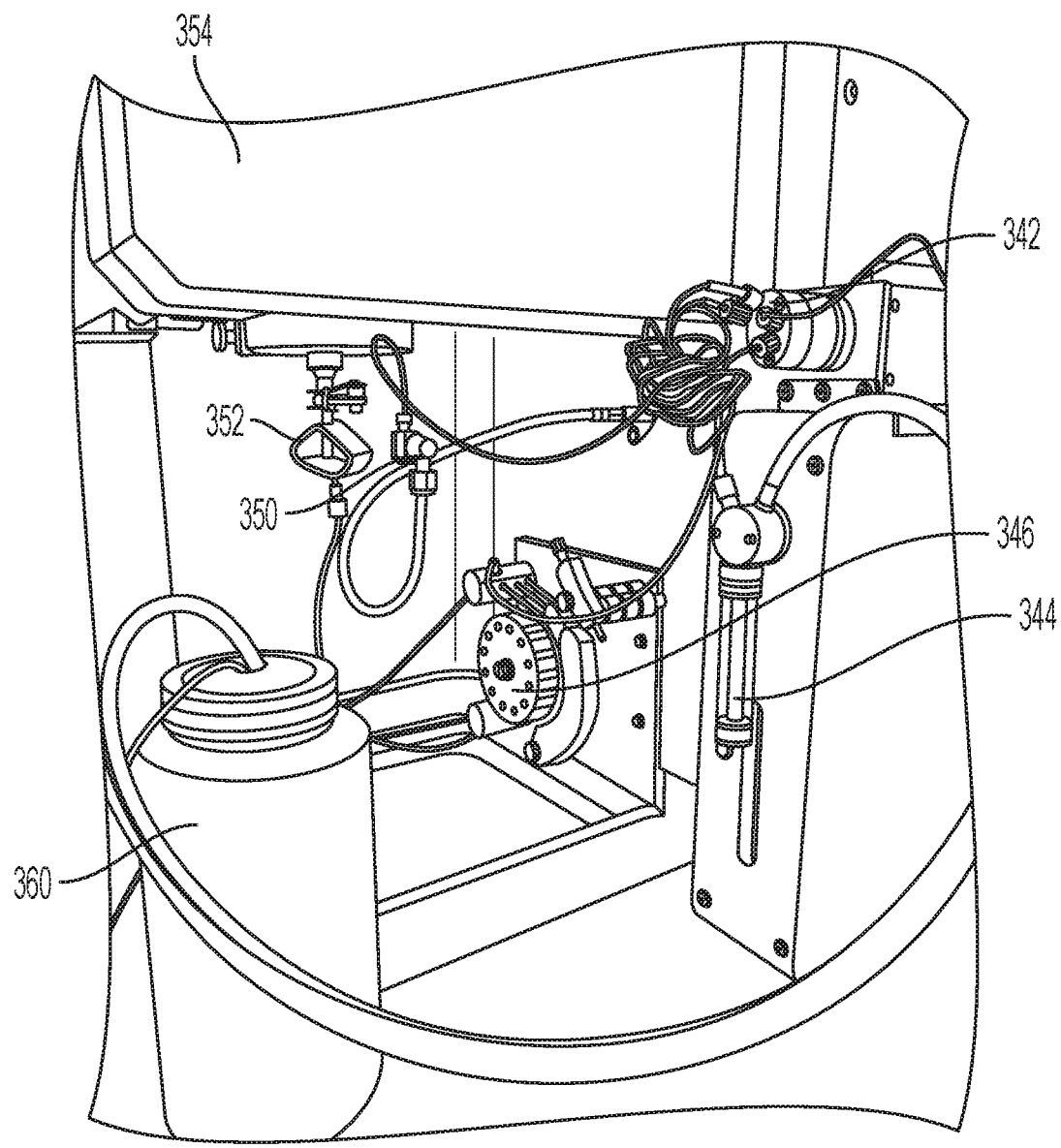
FIGS. 3A and 3B show detailed portions of FIG. 3.
Figure 3B:
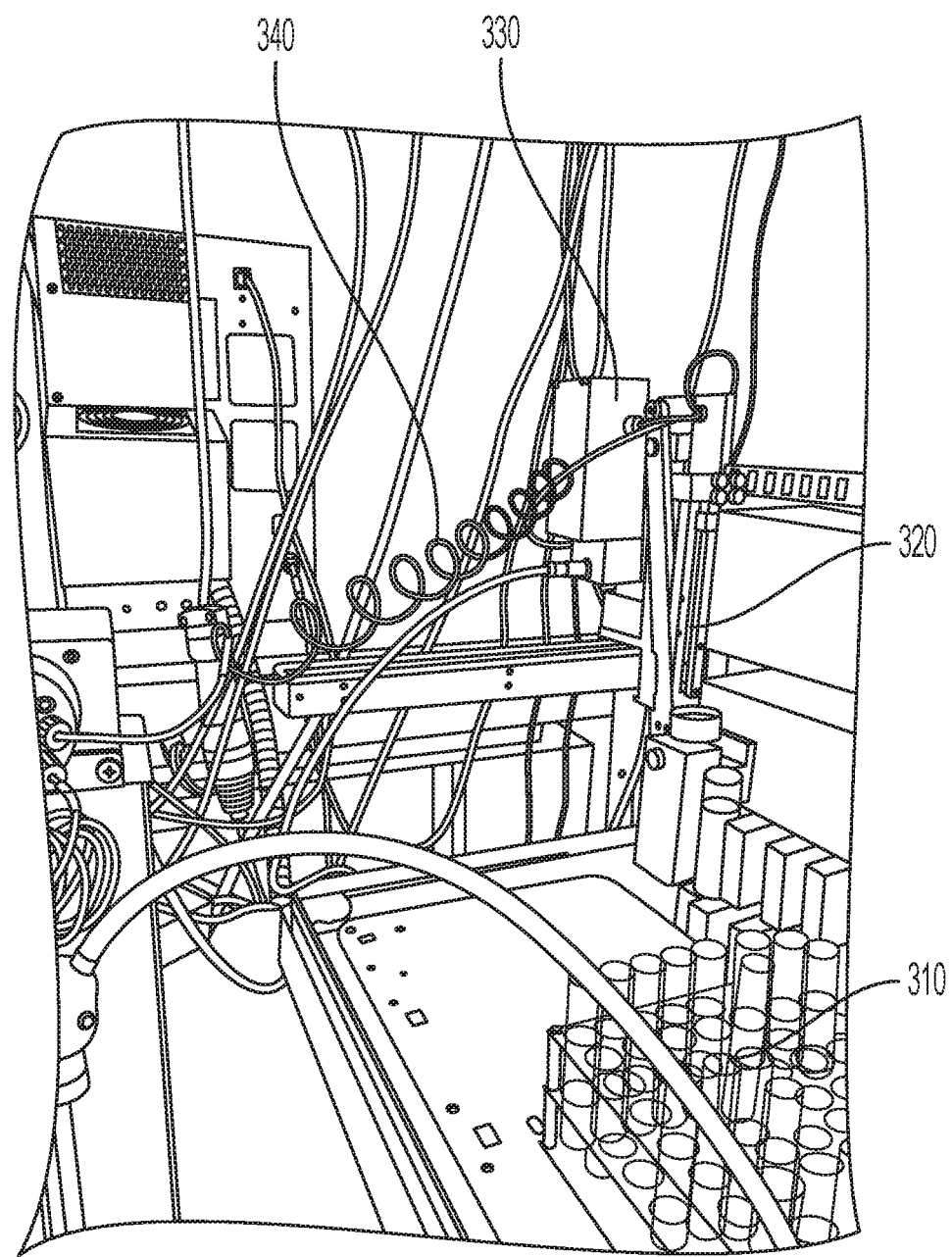

FIG. 3 and FIGS. 3A and 3B depict one possible arrangement of a particle counter and composition analyzer in a same system in accordance with one or more example embodiments. This figure depicts a delivery system (Autosampler)—CETAC 7400, a particle counter (Accusizer 7000), a feed system (Particle Express), and a composition analyzer (ICP-OES—Avio 500). Specifically a tray of sample tubes 310 are placed adjacent an aspiration probe with mesh 320. The aspiration probe delivers a sample to the particle sensor 330 in communication with the particle counter 332. The sample leaves the particle sensor through connection tube 340 and travels to a two position injection loop 342. A 10 mL syringe 344 operates as the feed mechanism for the particle counter (draws the sample through the particle counter) and the injection loop. A controller 348 controls the syringe and valves in the system. The two position injection loop 342 is filled by the syringe 344 and the loop content is transferred to the nebulizer 350 and spray chamber 352 via a carrier solution that is pumped through the sample loop by a peristaltic pump 346. The carrier solution 360 pushes the sample to the nebulizer 350 and spray chamber 352 then is used to rinse the sample from the nebulizer 350 and spray chamber 352 after the elemental analysis is completed by the ICP-OES 354.

Figure 4:
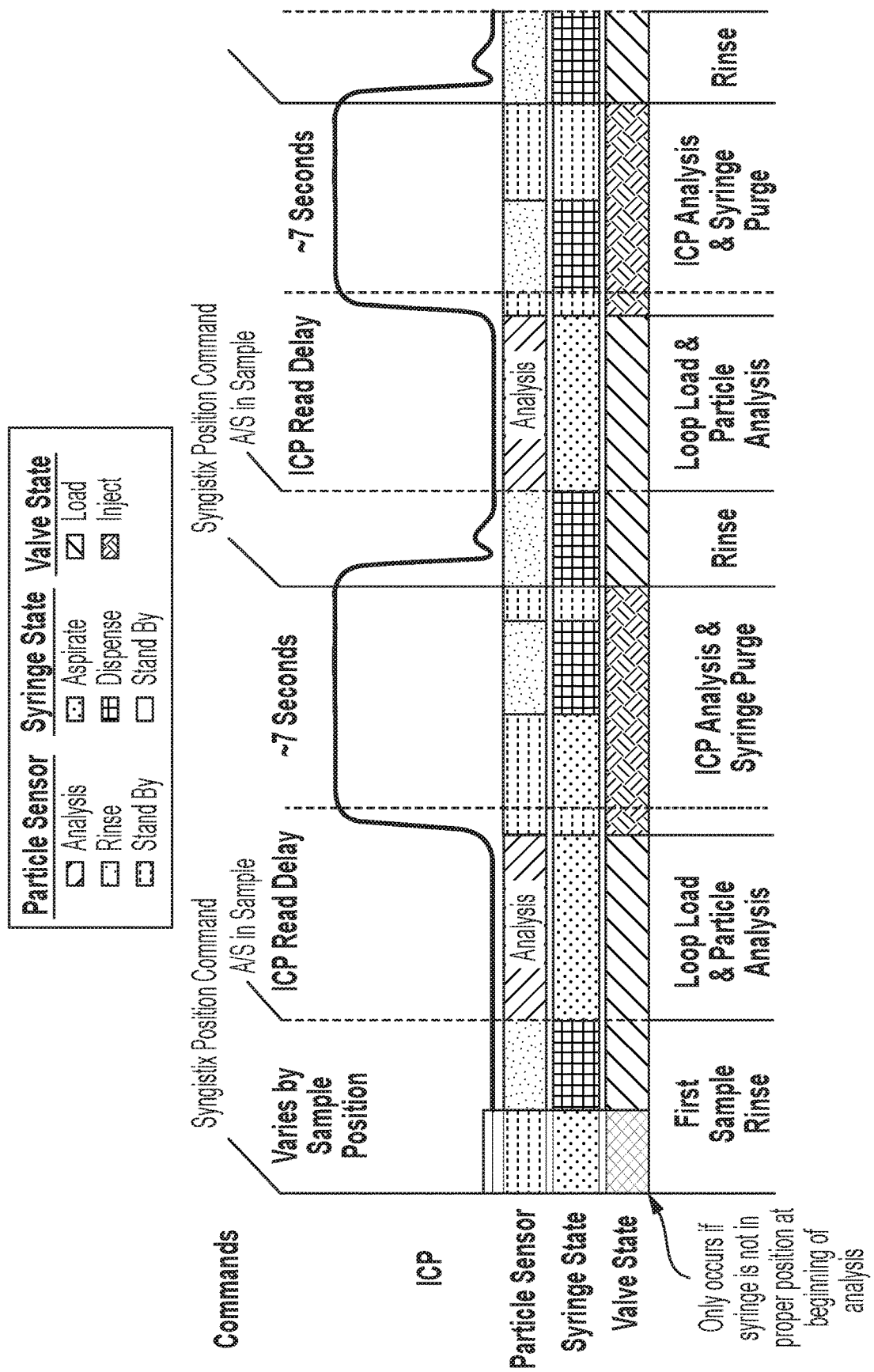
FIG. 4 depicts a system of analyzing liquid samples in accordance with one or more example embodiments.

An illustration of operational aspects of the present invention are depicted in FIG. 4. Particle sensors generally operate in three states: analysis, rinse, standby. The syringes generally operate in three states: aspirate, dispense, stand by. Valves operate in two states: load, inject.

Step 1: Sample Probe in Sample
1—Probe inserted in sample to be analyzed
2—Syringe pulls the sample to fill the particle sensor (determine particle size and number)
3—Syringe pulls the sample into injection loop Step 2: Particle Analysis is Completed
1—Valve switched to inject loop content into the ICP-OES
2—ICP-OES acquires sample, performs elemental analysis
3—Syringe and particle sensor are washed with rinse solution (syringe purge)

Step 3: Rinse
1—ICP-OES analysis complete—loop switch to load—Syringe content rinse solution is pushed through the loop for cleaning.

Once the particle-containing liquid sample is processed in the systems described herein, data generated by the data processing component 150 can be analyzed by techniques known to those of skill in the art, including techniques described in PerkinElmer U.S. Patent Application Publication No. 2015/0235833, the disclosure of which is incorporated herein in its entirety. In some aspects the data generated by the particle counter 120 can be correlated with the data generated by the composition analyzer 140 in order to further validate the results. Sample results can be output to an external data system (LIMS)). Output formats are typically CSV or TXT but other formats could be accommodated.

To simplify the process of determining the overall cleanliness of a lubricant many standards like ISO 4406, NAS 1638 have been created. The software can automatically report results in ISO 4406, NAS 1638, and many other standards.

It is to be understood that while illustrative particle counters and ICP-OES were used as examples of the analytical apparatuses herein, any other particle counters or composition analyzers are to be considered equivalent and may be used instead.

The particular configuration and operation of each analytical apparatus can vary from system to system, as can be appreciated by one of skill in the art. In certain embodiments of system 100, particle counter 120 and composition analyzer 140 may be separate instruments positioned proximate to one another and fluidically coupled, with composition analyzer 140 positioned downstream of particle counter 120 in-line. In certain other embodiments of system 100, the system 100 is implemented as an integrated instrument with particle counter 120 and composition analyzer 140 disposed within a single housing (not shown). For example, in some aspects particle counter 120 and composition analyzer 140, along with the feed system, for example, may be enclosed within housing such that their respective component parts are not exposed to the surrounding environment.

The present invention therefore combines particle counting and particle analysis, e.g., compositional (ICP) analysis of diluted samples; thus combining two separate analysis having two sample preparations to a single particle and elemental analysis using the same sample. By adding the particle counting in line with the diluted sample being fed to the composition analyzer as described, issues with viscous samples are eliminated thus allowing quick and easy analysis of lubricant samples, such as gear oils, transmission, steering fluid and hydraulics, or other normally viscous samples. The system provides fast sample analysis (e.g. 30 to 45 seconds per sample vs greater than 3 minutes for two separate samples), uses less sample for the analysis (e.g. less than 1 mL of sample vs. 20-30 mL), and less solvent (organic waste) since the particle counter is rinsed with the ICP solvent at the same time. All of these features bring very high value to these high-volume lubricant labs processing anywhere between 300 to 3000 samples per day improving efficiency and cost savings to these labs.

Although discussed in particular in terms of lubricants, the present application is directed to any types of fluids containing particles such as found in the food and beverage industries, aerospace industry, automotive industry, semiconductor industry, cosmetics industry, and healthcare industry.

Although the subject matter has been described in language specific to structural features and/or methodological acts, it is to be understood that the subject matter defined in the appended claims is not necessarily limited to the specific features or acts described above. Rather, the specific features and acts described above are described as example implementations of the following claims.

What is claimed is:

1. A system for analyzing a liquid sample, the system comprising:
    a liquid sample delivery system;
    a particle counter configured to receive a liquid sample from the liquid sample delivery system;
    a composition analyzer configured to receive the liquid sample from the particle counter;
    a feed system configured to draw the liquid sample through the particle counter and subsequently inject the liquid sample into the composition analyzer; and
    a processor to process and analyze data from the particle counter and composition analyzer.

2. The system of claim 1 wherein the feed system comprises a syringe and the liquid sample is pulled through the particle counter via the syringe.

3. The system of claim 1 wherein the feed system is configured to inject the liquid sample and a carrier into the composition analyzer.

4. The system of claim 3 wherein the feed system further comprises a pump and a carrier source, wherein the pump is configured to combine the liquid sample with a carrier prior to injecting into the composition analyzer.

5. The system of claim 4 wherein the pump is a peristaltic pump.

6. The system of claim 1 wherein the composition analyzer is an inductively coupled plasma optical emission spectrometry device (ICP-OES).

7. The system of claim 6 wherein the liquid sample is injected into a nebulizer of the ICP-OES.

8. The system of claim 1 further comprising a liquid sample preparation device configured to dilute a viscous source sample to form the liquid sample.

9. The system of claim 8 wherein the liquid sample preparation device dilutes the viscous source sample to a sample:liquid ratio of 1:1 to 1:20.

10. A method for analyzing a liquid sample, the method comprising:
    supplying the liquid sample containing particles to a particle counter;
    pulling the liquid sample through the particle counter via a feed system;
    analyzing the particles of the liquid sample for at least one of number and size;
    pulling the liquid sample into a sample loop after analyzing the particles;
    injecting the liquid sample from the sample loop into a composition analyzer;
    analyzing the liquid sample for its composition; and
    processing data from the particle counter and the composition analyzer;
    wherein a time period from feeding the liquid sample containing particles into the particle counter through analyzing the liquid sample in the composition analyzer is less than 45 seconds.

11. The method of claim 10 wherein the feed system includes a syringe, the method further comprising pulling the liquid sample through the particle counter via the syringe.

12. The method of claim 10 further comprising injecting the liquid sample and a carrier into the composition analyzer.

13. The method of claim 12 further comprising combining the liquid sample with a carrier prior to injecting the liquid sample into the composition analyzer.

14. The method of claim 13 wherein the feed system further comprises a peristaltic pump, wherein the carrier is pumped via the peristaltic pump into the composition analyzer.

15. The method of claim 10 wherein the composition analyzer is ICP-OES.

16. The method of claim 15 further comprising injecting the liquid sample into a nebulizer of the ICP-OES.

17. The method of claim 10 further comprising diluting a viscous source sample at a ratio of sample:liquid of 1:1 to 1:20 to form the liquid sample.

18. The method of claim 10 further comprising diluting a viscous source sample at a ratio of sample:liquid of 1:5 to 1:15 to form the liquid sample.

* * * * *